(12) United States Patent
McLaughlin et al.

(10) Patent No.: US 10,228,297 B2
(45) Date of Patent: Mar. 12, 2019

(54) DEVICE AND A METHOD FOR EVALUATING A MECHANICAL PROPERTY OF A MATERIAL

(71) Applicant: The University of Western Australia, Crawley (AU)

(72) Inventors: Robert Ainsley McLaughlin, Bayswater (AU); David Douglas Sampson, Claremont (AU); Brendan Francis Kennedy, Walliston (AU); Kelsey Marie Kennedy, Mosman Park (AU)

(73) Assignee: The University of Western Australia, Crawley, Western Australia (AU)

( * ) Notice: Subject to any disclaimer, the term of this patent is extended or adjusted under 35 U.S.C. 154(b) by 0 days.

(21) Appl. No.: 15/023,663

(22) PCT Filed: Jan. 29, 2016

(86) PCT No.: PCT/AU2016/000019
§ 371 (c)(1),
(2) Date: Mar. 21, 2016

(87) PCT Pub. No.: WO2016/119011
PCT Pub. Date: Aug. 4, 2016

(65) Prior Publication Data
US 2017/0328794 A1 Nov. 16, 2017

Related U.S. Application Data

(60) Provisional application No. 62/110,108, filed on Jan. 30, 2015.

(51) Int. Cl.
*G01L 1/24* (2006.01)
*A61B 5/00* (2006.01)
(Continued)

(52) U.S. Cl.
CPC .............. *G01L 1/24* (2013.01); *A61B 5/0053* (2013.01); *A61B 5/444* (2013.01); *G01B 11/16* (2013.01);
(Continued)

(58) Field of Classification Search
CPC ....... G01L 1/24; G01L 311/16; A61B 5/0059; A61B 5/721; A61B 5/442; A61B 5/444; G01B 11/16; G01N 3/00
See application file for complete search history.

(56) References Cited

U.S. PATENT DOCUMENTS 6,469,788 B2 * 10/2002 Boyd .................... G01N 21/211
356/369
7,127,950 B2 * 10/2006 Fonov ....................... G01L 1/24
73/800
(Continued)

FOREIGN PATENT DOCUMENTS

| CN | 103630272 | 3/2014 |
| KR | 20140118444 | 10/2014 |
| WO | 9850775 | 11/1998 |

OTHER PUBLICATIONS

Ruikang, Wang, "Tissue Dooppler optical coherence elastography for realtime strain rate and strain mapping of soft tissue", Aug. 9, 2006 American Institute of Physics.*
(Continued)

*Primary Examiner* — Maurice C Smith
(74) *Attorney, Agent, or Firm* — Michael Best & Friedrich LLP

(57) ABSTRACT

The present disclosure provides a device for evaluating a mechanical property of a material. The device comprises a sensing layer that has a contact surface for contacting a surface area of the material. The sensing layer has a property or dimension that is pressure sensitive. The device also comprises a detector arranged to detect electromagnetic
(Continued)

radiation that propagates through at least the sensing layer. The device is arranged such that, when the contact surface of the sensing layer is in contact with the surface area of the material and a load is applied on at least a portion of the surface area of the material, the detected electromagnetic radiation can be used to determine stress within a portion of the sensing layer, the determined stress being indicative of the mechanical property of the material.

11 Claims, 6 Drawing Sheets

(51) Int. Cl.
  *G01B 11/16*   (2006.01)
  *G01L 1/04*   (2006.01)
  *G01N 3/00*   (2006.01)
(52) U.S. Cl.
  CPC ............... *G01L 1/04* (2013.01); *G01L 1/241* (2013.01); *A61B 5/0059* (2013.01); *A61B 5/442* (2013.01); *A61B 5/4887* (2013.01); *A61B 2562/0266* (2013.01); *G01N 3/00* (2013.01)

(56) References Cited

U.S. PATENT DOCUMENTS

| | | | | |
|---|---|---|---|---|
| 2011/0302694 | A1* | 12/2011 | Wang | A61B 5/103 2/160 |
| 2013/0070074 | A1* | 3/2013 | Won | G01L 1/247 348/77 |
| 2014/0215684 | A1* | 8/2014 | Hardy | A41D 19/0031 2/160 |
| 2015/0130697 | A1* | 5/2015 | Keesling | G06F 3/014 345/156 |

OTHER PUBLICATIONS

International Search Report and Written Opinion for Application No. PCT/AU2016/000019 dated Apr. 19, 2016 (13 pages).
Es'Haghian et al., "Optical palpation in vivo: imaging human skin lesions using mechanical contrast", J Biomed Opt. (2015) vol. 20(1), 16013-01-016013-11.
Kennedy et al, "A review of optical coherence elastography: fundamentals, techniques and prospects", IEEE Journal of Selected Topics in Quantum Electronics, (2014) vol. 20(2), 272-288.
Kennedy et al., "Optical palpation: optical coherence tomography-based tactile imaging using a compliant sensor", Opt. Lett. (2014) vol. 39(10), 3014-3017.

* cited by examiner

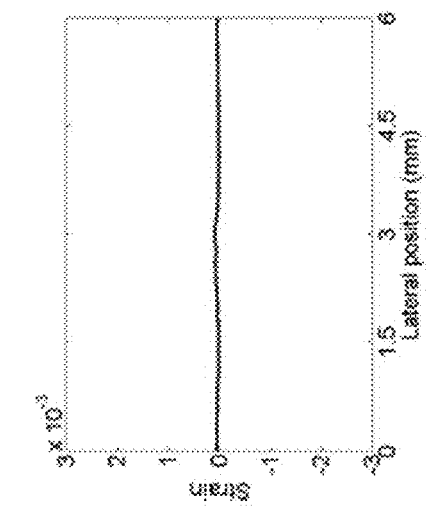
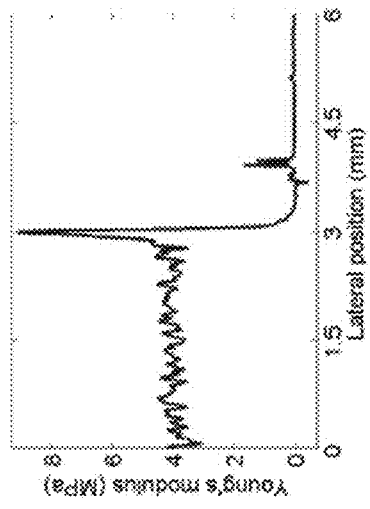
Figure 4a
Figure 4b
Figure 4c
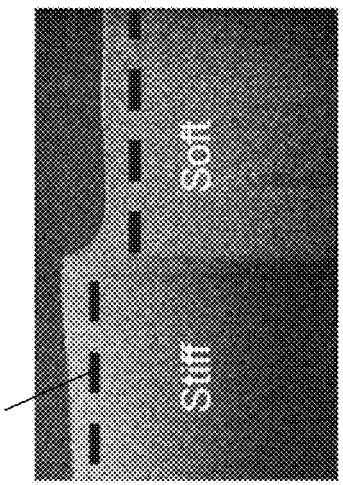
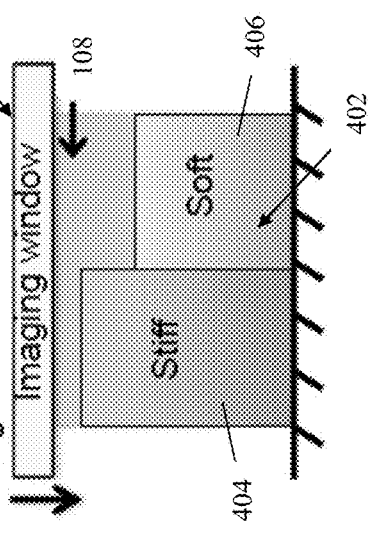
Figure 5a
Figure 5b
Figure 5c

DEVICE AND A METHOD FOR EVALUATING A MECHANICAL PROPERTY OF A MATERIAL

FIELD OF THE INVENTION

The present invention broadly relates to a device and a method for evaluating a mechanical property of a material, and relates particularly, not exclusively though, to a medical device and a method for evaluating elasticity of biological tissue.

BACKGROUND OF THE INVENTION

The mechanical properties of biological tissue are linked to its structure and function, and may be altered by disease. For example, cancerous tissue is usually "stiffer" than surrounding soft tissue and it is common practice that medical practitioners manually palpate the soft tissue of a patient by applying pressure with their fingers to identify the cancerous tissue.

However, the sense of touch is subjective and accurate identification of the extent of cancerous tissue using manual palpation is difficult. To provide mechanical contrast in tissue in a more repeatable, objective manner, imaging techniques have been developed, such as ultrasound elastography, optical coherence elastography and magnetic resonance elastography.

Despite the advent of these imaging techniques, medical practitioners still routinely resort to manual palpation in many clinical scenarios.

SUMMARY OF THE INVENTION

In accordance with a first aspect of the present invention, there is provided a device for evaluating a mechanical property of a material, the device comprising a sensing component which comprises:
  a sensing layer having a property or dimension that is pressure sensitive; and
  a receiver for electromagnetic radiation arranged to receive electromagnetic radiation that has interacted with at least a portion of the sensing layer;
  wherein the sensing component is arranged such that, when the sensing layer is positioned at a surface area of the material and a load is applied to both at least a portion of the surface area of the material and at least a portion of the sensing layer, received electromagnetic radiation that interacted with the sensing layer can be used to determine strain within at least the portion of the sensing layer, the determined strain being indicative of the mechanical property of the material.

The term "material" as used herein is intended to encompass any matter that has a mechanical property such as elasticity or viscoelasticity, including, for example, biological material such as biological tissue, organic materials such as food, and non-biological material such as a silicone material or the like.

The sensing layer may have a known stiffness and the electromagnetic radiation may then be used to determine stress from the determined strain.

The device may be arranged such that the strain within at least a portion of the sensing layer can be determined using reflected electromagnetic radiation reflected at interfaces of or within the sensing layer, such as top and bottom interfaces or internal interfaces if the sensing layer comprises a layered structure.

The sensing layer may be arranged for direct or indirect contact with the surface area of the material.

The device may also be arranged to determine strain within a portion of the material such that the mechanical property of the material can be evaluated using the determined strain within the portion of material and the determined stress within the portion of the sensing layer. For example, the portion of the material may comprise an outer layer portion of the material or another suitable portion of the material.

Embodiments of the invention provide significant advantages. For example, by determining the stress at the sensing layer, due to the knowledge of the material properties of the sensing layer, qualitative information in relation to the mechanical property of the material can be determined, such as a relative variation of the mechanical property across an area of the material. In the medical field, the device may provide an optical palpation technique in which the sense of touch of the manual palpation is replicated. In addition to the sense of touch, the device may provide objectivity, high spatial resolution and high sensitivity to changes in the mechanical property of the material. In this way, for example the accuracy of locating the extent of diseased tissue may be improved and the device may be used to guide a surgeon.

The device may comprise an element for attaching the sensing component to a member such that movement or positioning of the sensing component can be controlled via the member. The member may be a body portion of a user whereby the element with the sensing component is wearable by the user. The body portion may be at least portion of a hand, such as finger, of the user. The element may surround at least partially the body portion.

In one specific embodiment the element is a glove or a thimble. The sensing component may be positioned at or attached to a tip of one or more finger portions of the glove or at a tip of thimble. This provides advantages in the medical field. For example, by incorporating or attaching the sensing component to one or more fingers portions of the glove or to the thimble, manual palpation may be simultaneously performed with the optical palpation performed by the device when the glove or the thimble is worn by a user and the fingertip is moved along the material, which may be biological tissue.

Alternatively, the element may for example be a clip or the like.

In an alternative embodiment, the device comprises a probe, such as an elongated probe. In this embodiment, the sensing component may be incorporated in or attached to a distal end portion of the probe. The probe may for example be at least one of: a handheld probe, an elongated probe, an endoscopic probe, an intravascular probe, a robotic arm and a needle probe such as a biopsy needle probe. In this regard, the device may be controlled remotely. For example, sensing component may be attached to a robotic arm which is controlled remotely. In the medical field, the sensing component may be positionable such that a relative variation of a mechanical property of biological tissue can be evaluated at a location that may not be accessible using manual palpation. For example, the device may be usable for minimally invasive surgery.

In one specific embodiment of the present invention the sensing component is arranged for manual application of the load. The sensing component may be arranged such that, when the user wears the sensing component and the element, the user can apply the load manually via the sensing layer (for example by pressing with a finger) to the surface of the area at the material.

In an alternative embodiment of the present invention the sensing component may comprise an actuator for applying the load. The actuator may be arranged to generate a uniform or alternating load.

The load typically is a compressive load. However, other types of loads are envisaged, such as indentation, suction, shear, photothermal, air puff, acoustic radiation force, torsion, and extension. The load may be static or dynamic.

The mechanical property may relate to an elasticity of the material, such as an elasticity of biological tissue. For example, the mechanical property may relate to the Young's modulus or other modulus of the material. Alternatively, the mechanical property may relate to a viscoelasticity or any other mechanical property.

In an embodiment, the sensing layer is compliant. Specifically, the sensing layer may be arranged to conform to the surface area of the material. In particular, the sensing layer may be deformable at least along a thickness of the sensing layer. Further, the sensing layer typically is resilient at least along the thickness of the sensing layer. If the load is applied to the portion of the surface area via the sensing layer, a compliant sensing layer facilitates a substantially even transfer of the load to the material. As a consequence, air gaps between the sensing layer and the surface area of the material can be reduced.

The device may be arranged such that the sensing layer is deformed at least along the thickness of the sensing layer in response to the load applied to at least the portion of the surface area of the material. In this regard, the received electromagnetic radiation may be used to determine a deformation of the sensing layer, for example to determine the thickness of the sensing layer during application of the load. In this regard, the electromagnetic radiation may be deflected or reflected at interfacial regions of the sensing layer. For example, the device may be arranged to employ interferometry, such as low coherence interferometry, to determine a relative position of top and bottom interfaces of the sensing layer.

The sensing layer may be transmissive for at least the detected electromagnetic radiation.

The sensing layer may at least partially be composed of a silicone material. However, other materials and composition of materials are envisaged.

In one embodiment, the device comprises a light source arranged to emit electromagnetic radiation into at least the sensing layer. In particular, the light source may be arranged to direct the electromagnetic radiation into the material through the sensing layer.

The receiver may be a detector for the electromagnetic radiation. Alternatively, the device may comprise a detector that is separate from the receiver. The receiver may also be arranged for emission of electromagnetic radiation from the light source and into the sensing layer.

In an embodiment, the device is arranged to employ at least one of: optical coherence tomography, confocal fluorescence microscopy, optical coherence elastography.

In one particular example the emitted electromagnetic radiation is infrared light such as near-infrared light.

In a specific embodiment, the device is arranged to determine the mechanical property of the material. For example, a Young's modulus or any other suitable modulus of the material may be determined. In this regard, the device or a corresponding further device may be arranged to determine strain within the material, for example by using optical coherence elastography (OCE). A relation between the determined strain and the stress determined at the portion of the sensing layer may be calculated such that the mechanical property of the material can be quantitatively determined.

In one example, the device is arranged such that the sensing layer is removable.

In an embodiment, the device comprises an array of detectors such that stress at lateral positions across an area of the contact surface can be determined. For example, the device may comprise a bundle of optical fibres including fibres having ends that are distributed across an area associated with the above mentioned lateral positions.

In an alternative embodiment, the device is arranged to laterally scan across an area of the sensing layer such that stress at lateral positions across the area of the sensing layer can be determined. For example, the device may comprise a scanning mirror, such as a galvanometer mirror.

With the above mentioned embodiments, a 2D or 3D strain map or a 2D or 3D stress map may be generated indicating variations of the mechanical property across an area of the material.

In a specific embodiment, the device is a medical device and the material is biological tissue, such as soft tissue of a human or an animal. The soft tissue may be accompanied by, or may comprise diseased tissue such as cancerous tissue. Specific examples for soft tissue may be connective tissue, tendon, fat and muscle tissue.

For the ease of understanding, the term "diseased" is used throughout the patent specification as a synonym for an abnormality in the tissue including, for example, a lesion or a tumour that may be benign, pre-malignant, malignant, or any other diseased or abnormal state.

Alternatively, the material may be non-biological material such as silicone or any other suitable material.

The device may further be arranged to use information in relation to the mechanical property, such as a relative variation of the mechanical property across an area, to identify a location of an interface between two different types of material portions. For example in the medical field, the device may be arranged to identify presence or absence of diseased biological tissue. In this way, the extent of diseased tissue may be identified.

In accordance with a second aspect of the present invention, there is provided a method of evaluating a mechanical property of a material, the method comprising:
  providing a material;
  positioning a sensing layer at a surface area of the material such that a load can be applied to both at least a portion the material and at least a portion of the sensing layer at the surface area of the material, the sensing layer having a property or dimension that is pressure sensitive;
  applying the load to both at least a portion of the surface area of the material and at least a portion of the sensing layer at the surface area of the material;
  emitting electromagnetic radiation into at least a portion of the sensing layer when the load is applied;
  receiving electromagnetic radiation that has interacted with at least a portion of the sensing layer; and
  determining strain at a portion of the sensing layer using the received electromagnetic radiation, the determined strain being indicative of the mechanical property of the material.

The method may comprise attaching a sensing component to a member using an element for attaching the sensing component such that movement or positioning of the sensing component can be controlled via the member, the sensing component comprising a sensing layer and a receiver for electromagnetic radiation. The member may be a body portion of a user body portion of a user such that the user wears the element and the sensing component. For example, the sensing layer may be incorporated in or attached to a finger portion of a glove or a thimble. In this example, the step of applying the load to at least the surface area of the material may comprise applying pressure via the sensing layer using one or more fingers of a user. Alternatively, the element for attaching the sensing component may for example be a clip.

The step of attaching a sensing component to the body portion may comprise surrounding at least partially the body portion.

The sensing layer may have a known stiffness and the method may comprise determining stress from the determined strain.

The step of receiving the electromagnetic radiation may comprise detecting the electromagnetic radiation.

The step of applying the load may comprise applying the load manually or using an actuator that may apply a static or dynamic load. In one specific embodiment the step of applying the load comprises applying the load manually by a user who wears the sensing component with the element.

The step of detecting electromagnetic radiation that has interacted with at least a portion of the sensing layer may comprise detecting electromagnetic radiation that was reflected at interfaces of or within the sensing layer, such as top and bottom interfaces or internal interfaces if the sensing layer comprises a layered structure.

The step of positioning the sensing layer at the surface area of the material may comprise positioning the sensing layer such that the sensing layer is in direct or indirect contact with the surface area of the material.

The step of applying the load may comprise applying the load through the sensing layer.

In an embodiment, the sensing layer is incorporated in, or attached to, a distal end of a probe and the step of positioning the sensing layer comprises inserting the distal end of the probe including the sensing layer into a body lumen or blood vessel for an intravascular analysis. For example, the distal end of the probe may be inserted through an incision for minimally invasive surgery. In this embodiment, movement of at least the distal end of the probe may be controlled remotely. In a further example, the sensing layer may be incorporated in or attached to a distal end of a needle probe. For example, the sensing layer may be positioned at the blunt distal end of an inner needle that is accommodated within an outer needle for inserting the needle probe into biological tissue. In other examples, the distal end of the probe is inserted into a tendon or cartilage to conduct an orthopaedic analysis, or into an ear canal to conduct an otoscopic analysis. It will be appreciated by a person skilled in the art that other suitable examples are envisaged.

In an embodiment, the method may be conducted in vivo, for example during surgery of a patient.

In an embodiment, the method may further comprise facilitating guidance for positioning the contact surface of the sensing layer in contact with the surface area of the material. For example, the method may comprise a step of capturing images of at least the surface area of the material.

In an embodiment, the step of determining stress at a portion of the contact surface of the sensing layer comprises determining a deformation of the sensing layer in response to the application of the load. Specifically, the step may comprise determining a thickness of the sensing layer. In this regard, the step of emitting the electromagnetic radiation into at least the sensing layer is conducted such that the electromagnetic radiation is deflected or reflected at an edge of the sensing layer.

The step of determining the thickness of the sensing layer may be conducted before and/or after the load is applied to at least the portion of the surface area of the material.

In one embodiment, the step of emitting the electromagnetic radiation comprises directing the electromagnetic radiation into the material through the sensing layer.

In a specific embodiment, the method comprises a step of determining the mechanical property of the material, such as the Young's modulus. In this regard, the method may comprise a step of determining strain within the material, for example by using optical coherence elastography (OCE). A relation between the determined strain and the stress determined at the portion of the sensing layer may be calculated such that the mechanical property of the material can be quantitatively determined.

In an embodiment, the step of receiving electromagnetic radiation that has propagated through at least the sensing layer comprises detecting electromagnetic radiation from a plurality of lateral positions by laterally scanning across an area of the sensing layer.

The method may further comprise a step of generating a 2D or 3D strain map, or 2D or 3D stress map indicating variations of the mechanical property across an area of the material.

The method may further comprise a step using information in relation to the mechanical property to identify presence or absence of diseased biological tissue.

In one embodiment, the method is conducted using the medical device in accordance with the first aspect of the present invention.

In accordance with a third aspect of the present invention, there is provided method of evaluating a mechanical property of a material using optical coherence tomography (OCT) or any other imaging technique, the method comprising the steps of:

positioning a material layer on a surface portion of the material, the material layer being transmissive for radiation that is used in the OCT or any other imaging technique;

applying a load to a surface portion of the material via the layer; and receiving radiation from the material to evaluate the property using the OCT or any other imaging technique when the load is applied to the surface portion of the material;

wherein the layer has a mechanical property that allows substantially even distribution of the load over the surface portion of the material.

The invention will be more fully understood from the following description of specific embodiments of the invention. The description is provided with reference to the accompanying drawings.

BRIEF DESCRIPTION OF THE DRAWINGS

FIG. 4a is an excerpt of an exemplary setup for performing an OCE measurement;

FIGS. 4b and c show data acquired using the exemplary setup of FIG. 4a;

FIG. 5a is an excerpt of the medical device of FIGS. 1a and b;

FIGS. 5b and c show data acquired using the exemplary setup of FIG. 5a;

FIGS. 7a and b show data acquired using the medical device in accordance with the schematic representation of FIG. 6a.

DETAILED DESCRIPTION OF SPECIFIC EMBODIMENTS

Figure 1A:
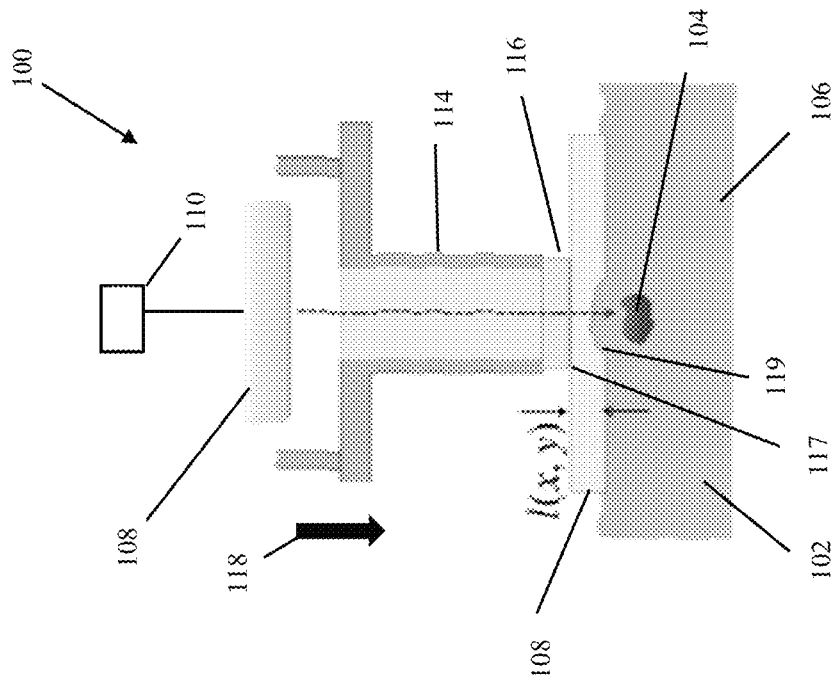
FIGS. 1a and b are schematic representations of a medical device for evaluating a mechanical property of a material in accordance with an embodiment of the present invention.

Embodiments of the present invention relate to a device and a method for evaluating a mechanical property of a material. The device may for example be a medical device. In this case, the material may be biological material, such as biological tissue. However, non-biological material is envisaged such as silicone material that is typically used for replicating the form and structure of biological soft tissue in the medical field.

It will be appreciated by a person skilled in the art that the device has applications not only in the medical field but also in various other fields including for example robotics and the food industry. The mechanical property may be evaluated for any suitable material that is compliant. For example, in the food industry, the device may be used to determine the ripeness of food. Further, the device may be used in quality control applications and for material processing.

The mechanical property typically relates to the elasticity of the material. Specifically, the elasticity may relate to a Young's modulus of the material. The Young's modulus is representative of the stiffness of the material. In the medical field, it has been known that abnormalities such as diseased tissue may alter the elasticity of biological tissue. For example, cancerous tissue typically feels "stiffer" than surrounding healthy soft tissue. This difference in elasticity of biological tissue has conventionally been used in identifying the presence or absence of cancerous tissue by the use of manual palpation. However, this technique is subjective to the medical practitioner who performs the manual palpation. Also, the exact extent of cancerous tissue may be difficult to identify by merely using manual palpation.

In the following, exemplary embodiments of the device and the method in the medical field will be described. However, as mentioned above, applications in other technology fields are envisaged.

The medical device in accordance with embodiments of the present invention is arranged to evaluate the elasticity of the biological tissue by determining stress at a portion of a sensing layer of the medical device that in use is in contact with a surface area of the biological tissue. In this way, a variation of the elasticity of the biological tissue across an area may be qualitatively determined and thereby a location of cancerous tissue identified.

With regard to the mechanical property of the material, it will be appreciated that other mechanical properties are envisaged, such as viscoelasticity of the material.

The medical device in accordance with embodiments of the present invention comprises a sensing component that includes a sensing layer and a detector. The detector is arranged to detect electromagnetic radiation that has propagated through the sensing layer. The medical device comprises in this embodiment also an element that can be used to attach the sensing component to a body portion of a user. For example, the body portion may be a finger or a hand of the user and the element may be a thimble or a glove that the user can wear with the sensing component.

Electromagnetic radiation may be emitted into the material through the sensing layer such that the electromagnetic radiation is deflected or reflected at top and bottom edges of the sensing layer. The detected electromagnetic radiation is used to determine stress experienced at a portion of the above mentioned sensing layer.

The sensing layer has a property or a dimension that is pressure sensitive, and has a contact surface for contacting a surface area of the material, such as a skin surface area of biological tissue. When a load is applied to the material and the sensing layer is in contact with the surface area of the material, the stress that is determined at the portion of the sensing layer can then be used to evaluate the mechanical property of the material. In this way, a variation of the mechanical property of the material across an area below the surface area of the material can be qualitatively determined. In order to quantitatively determine the mechanical property of the material, a further measurement may be required that is combined with the determined stress. For example, the medical device may be arranged to employ OCE to determine strain distributed within the material. By calculating a relation between the strain of the material and the stress at the sensing layer, the Young's modulus of the material can be quantitatively determined.

The medical device may find applications in locating the presence and extent of diseased tissue. In some examples, the sensing layer forms part or is attached to one or more finger portions of a glove or is attached to a thimble. In this way, manual palpation performed by a medical practitioner may be simultaneously performed with optical palpation using the medical device.

In a further example, the medical device comprises a probe, such as an endoscopic probe, a needle probe or an intravascular probe. In such an embodiment, the sensing layer may be part or attached to a distal end of the probe so that the sensing layer can be inserted into a body lumen. In this way, the medical device can be used for minimally invasive surgeries.

Referring now to FIGS. 1a and b, there is shown schematic representations of a medical device 100 for evaluating a mechanical property of a material 102 in accordance with an embodiment of the present invention.

In this particular example, the mechanical property of the material 102 relates to elasticity. The material 102 is a compliant silicone material 102 that is typically used to replicate the structure and form of biological soft tissue. The silicone material 102 comprises an inclusion 104 that is stiffer than the surrounding silicone material 106. In this regard, the inclusion 104 may represent a tumour and the surrounding silicone material 106 may represent surrounding soft tissue.

In this example, the inclusion 104 has a Young's modulus E of 1.5 MPa and is embedded approximately 1 mm below the surface area of the material. The surrounding silicone material 106 has a Young's modulus E of 20 kPa. The Young's modulus is representative of the stiffness of the silicone material 102.

The medical device 100 may be used in vivo to locate the presence and extent of diseased tissue such as a tumour within healthy soft tissue. In this particular example, by evaluating a variation in elasticity of the silicone material 102 across an area below the surface, it is possible to identify the location and extent of the inclusion 104 within the surrounding silicone material 106.

The medical device 100 comprises a sensing layer 108 and an optical system 110.

In this example, the optical system 110 comprises a light source for emitting electromagnetic radiation and a detector for detecting electromagnetic radiation that has interacted with at least a portion of the sensing layer. For example, the electromagnetic radiation may be reflected, deflected or scattered from a boundary of the sensing layer. However, a person skilled in the art will appreciate that the light source may not be part of the medical device 100.

The optical system 110 in this embodiment is in the form of an optical coherence tomography ("OCT") system 110. In particular, a portable swept-source OCT system 110 is used with a central wavelength of 1325 nm (near-infrared) and a spectral bandwidth of 100 nm. The measured axial and transverse resolutions (full width and half-maximum) of the OCT system 110 are 17 µm (in air) and 16 µm, respectively. With regard to OCT systems, it will be appreciated that any suitable OCT system may be used for the medical device 100. For example, the OCT system may be a spectral-domain OCT system with central wavelength of 840 nm and a spectral bandwidth of 50 nm. The axial and transverse resolutions of this exemplary system are 8 µm and 11 µm, respectively. Furthermore, the OCT system may be a phase sensitive swept-source OCT system.

Electromagnetic radiation emitted from the OCT system 110 illuminates the surface area of the silicone material 102 through a lens 112 with a working distance of 25 mm. The electromagnetic radiation is directed into a portion of the silicone material 102 through the lens 112 and the sensing layer 108. However, it will be appreciated that the electromagnetic radiation may alternatively propagate through the material before propagating through the sensing layer 108.

The sensing layer 108 has a contact surface that in this embodiment in use is in contact with a surface area of the silicone material 102 as shown in FIGS. 1a and b. In this particular example, the sensing layer 108 is composed of a silicone material. However, other suitable materials or material compositions are envisaged. In the example of silicone material, it should be noted that the properties of the silicone material may be controlled by altering ratios of silicone catalyst, cross-linker and non-cross linked silicone fluid.

Figure 1B:
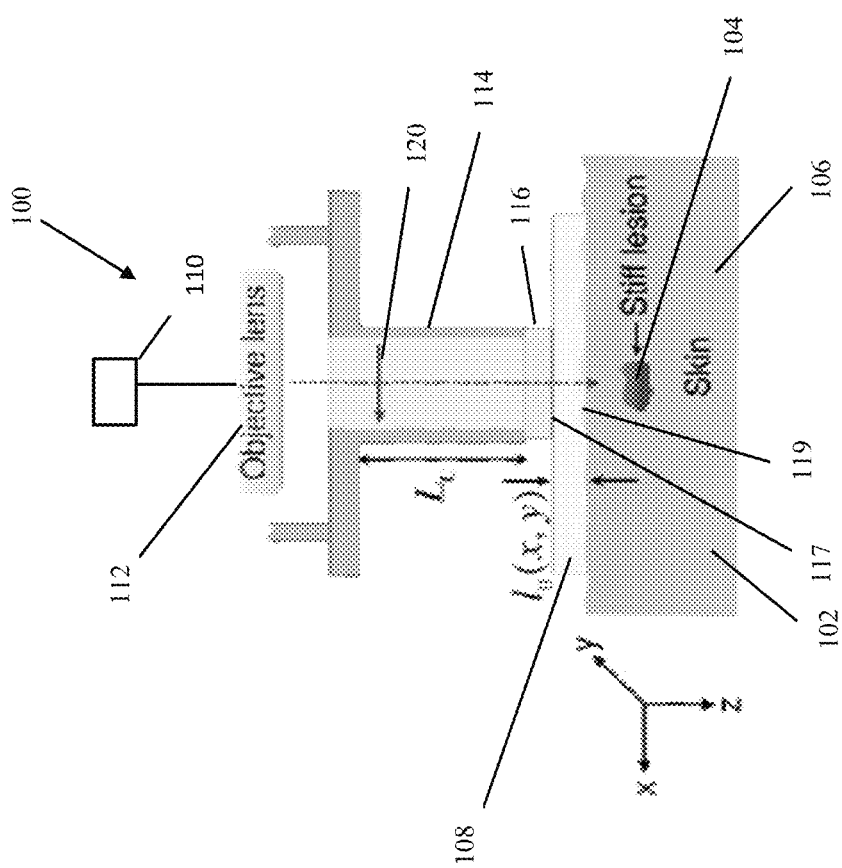

The sensing layer 108 of the medical device has a property or a dimension that is pressure sensitive. In this specific example, the sensing layer 108 is deformable across the thickness of the sensing layer 108 and is resilient. The sensing layer 108 has a Young's modulus that is in the range of the surrounding silicone material 106 of the silicone material 102, i.e. approximately 20 kPa. This allows the sensing layer 108 to conform to the structure of the surface area of the material and to deform when a load is applied to the surface area of the material as shown in FIG. 1b.

The load in this example is a compressive load that is applied using the medical device 100. In particular, the medical device 100 has a cylindrical head 114 with an anti-reflection coated imaging window 116. The imaging window 116 functions as a compression plate to apply the load to the surface area of the biological tissue 102 via the sensing layer 108 as illustrated by arrow 118 in FIG. 1b.

The length of the cylindrical head 114 is set to maximise the measurable displacement range of the medical device 100 and thereby the compression of the biological tissue 102. Maximising the range of displacement is of particular importance for locations in which the diseased tissue is located relatively far below the surface area of the tissue, for example in cases in which the biological tissue has relatively thick subcutaneous fat. In such a case, a larger displacement is necessary to adequately compress the biological tissue 102 so that the elasticity of the biological tissue below the surface area can be evaluated.

With regard to the application of the load, it will be appreciated that the load may be any suitable load, such as indentation, suction, shear, photothermal, acoustic radiation force, air jet, torsion or extension. Furthermore, the load may only be applied to the portion of the surface area of the material such that the sensing layer can conform to the profile of the surface area of the material.

When the load is applied to the portion of the surface area of the silicone material 102 as shown in FIG. 1b, the sensing layer 108, which has an interface 117 with the imaging window 116 and an interface 119 with material 102, at least partially deforms at the contact surface of the sensing layer 108. In other words, the thickness of the sensing layer 108 changes in response to an application of the load to the portion of the surface area of the silicone material 102.

In this example, the distance between the axial location of the upper and lower edges of the sensing layer 108 is determined using the OCT system 110. In particular, the electromagnetic radiation that is emitted into the sensing layer is reflected by the top and bottom edges of the sensing layer 108. In this example, low coherence interferometry is employed to determine the distance between the top and bottom edges of the sensing layer 108.

As shown in FIG. 1b, due to deformation of the sensing layer 108, the thickness of the sensing layer 108 changes in response to an application of the load. Due to the configuration of the exemplary OCT system 110, the minimum measurable change in thickness of the sensing layer 108 is approximately 4 µm. It will be appreciated by a person skilled in the art that other OCT systems may be used for measuring smaller changes. For example, for changes in thickness of the scale of 1 nm, the phase sensitive capability of an OCT system may be used.

The determined deformation of the sensing layer 108 is then used to determine stress experienced at a portion of the sensing layer 108. In this example, for determining the stress experienced at the portion of the sensing layer 108, the strain ε is determined as follows:

$$\varepsilon(x, y) = \frac{l(x, y) - l_0(x, y)}{l_0(x, y)}$$

wherein ε relates to the strain of the silicone material, $l_0$ relates to the thickness of the sensing layer 108 before application of the load, $l$ relates to the thickness of the sensing layer 108 after application of the load, and (x,y) relates to a lateral position across an area of the sensing layer 108.

In this example, the thickness of the sensing layer 108 is determined before application of the load. However, it will be appreciated that the thickness may alternatively be determined after application of the load or not at all as the normal thickness of the sensing layer 108 may be known.

Figure 2:
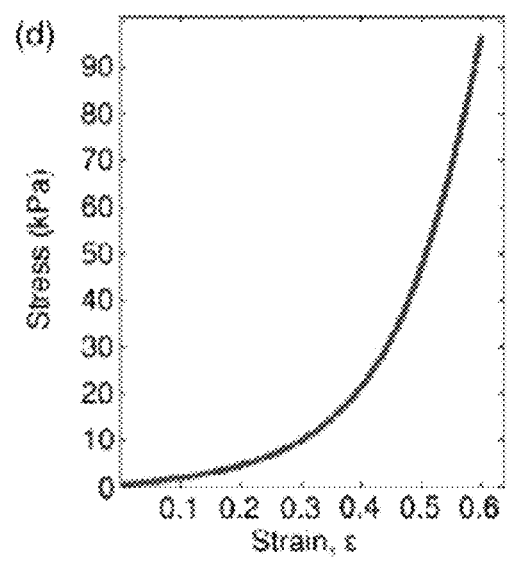
FIG. 2 shows a stress-strain curve used to determine the stress at a portion of the sensing layer of the medical device of FIGS. 1a and b.

To determine the stress, a stress-strain curve of the material of the sensing layer 108 is used as exemplarily shown in FIG. 2. Using the stress-strain curve of the particular material of the sensing layer 108, the stress experienced at the portion such as an area of the sensing layer 108 can be determined.

The stress at the portion of the sensing layer 108 is indicative of the elasticity of the material. By evaluating the elasticity across an area of the silicone material 102, a 2D stress map may be generated. An example of a 2D stress map is exemplarily shown in FIG. 3. A 3D stress map may additionally be created by acquiring a series of 2D stress maps with increasing loads or by incorporating the 2D stress into a computational mechanics model.

The stress map corresponds to an area for which the stress is determined using the medical device 100. In this regard, the OCT system 110 is arranged to scan across an area, for example line by line in a direction indicated by arrow 120. This may be implemented by providing a scanning mirror. However, in an alternative embodiment, the medical device 100 may comprise an array of detectors for detecting electromagnetic radiation in response to electromagnetic radiation that is directed to a plurality of respective locations, for example, using an optical fibre bundle.

Figure 3:
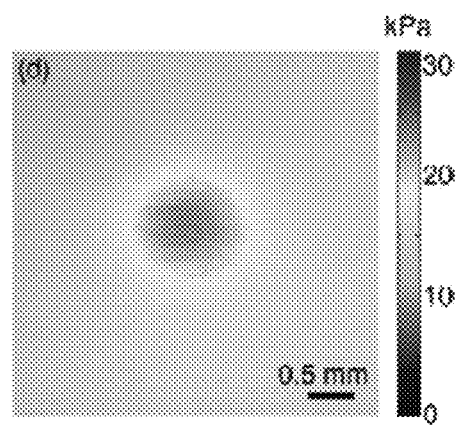
FIG. 3 shows an exemplary stress map acquired using the medical device of FIGS. 1a and b.

The lateral resolution of the stress map is approximately 160 to 390 μm which is in the sub-millimeter range. The upper limit on achievable resolution is set by the OCT system resolution. The resolution is dependent on both the resolution of the OCT system 110 and is influenced by the structural and mechanical heterogeneity within the biological tissue. However, it should be noted that the mechanical contrast represented by the stress map shown in FIG. 3 is independent of optical properties of the material, such as the silicone material or biological tissue. For example, a variation in elasticity of the material may be evaluated in the presence of for example blood.

The medical device 100 in accordance with this embodiment of the present invention may be able to evaluate the elasticity of the material 102 in a depth that is beyond the maximum depth of conventional OCT imaging techniques. The imaging depth of OCT is typically 1-2 mm below the surface. However, the medical device may evaluate the elasticity of the material at a depth lower than 2 mm below the surface. In an experiment, the medical device 100 was used to locate an inclusion that was embedded into silicon material at 4 mm depth below the surface. When the load was applied, the inclusion was located at approximately 3.7 mm below the surface.

In a particular example, the medical device 100 further comprises a glove or a thimble such that the sensing layer is incorporated in or attached to one or more finger portions of the glove or is attached to the thimble. In this case, the load may be applied by applying pressure with one or more fingers.

The medical device 100 may further comprise an optical light guide such as an optical fibre that connects the sensing layer 108 and the OCT system 110. For the example of the medical glove, the sensing layer may be incorporated in or attached to a finger cap, such as a plastic or metal thimble. A groove may be provided within the thimble such that a bundle of optical fibres can be guided to the tip of the one or more finger portions to establish optical coupling. In this way, a 2D image indicative of the elasticity of the tissue can be generated.

Thus, the medical device 100 provides an optical palpation system with which the assessment using manual palpation may be combined.

A person skilled in the art will appreciate that in an alternative embodiment of the medical device may comprise an actuator that is arranged to generate the load. The load may be static or dynamic.

The medical device 100 may also comprise a probe such an endoscopic probe, needle probe or an intravascular probe. In this way, the elasticity of biological tissue may be evaluated in vivo at a location that may not be accessible using manual palpation. For example, the medical device 100 may find application in the field of robotics surgery, such as minimally invasive surgery. In this regard, at least the sensing layer of the medical device may be attached to a distal end of an elongated probe that can be passed through an incision, for example through a wall portion of a patient's abdominal.

Positioning the medical device 100 relative to a surface area of biological tissue may be controlled remotely. For example, the medical device 100 may comprise or be connected with an image capturing device such as a camera such that the contact surface of the sensing layer can be brought in contact with a surface area of the biological tissue in question.

Referring now to FIGS. 4 and 5, there is illustrated a comparison between an optical coherence elastography ("OCE") setup using a medical device 200 (FIG. 4*a*) that is similar to medical device 100 of FIG. 1 but without a sensing layer and the medical device 100 (FIG. 5*a*). In this particular example, instead of a swept-source OCT system, a spectral domain system is used. However, any suitable OCT system is envisaged to perform the quantitative measurement.

Fundamentals and techniques of optical coherence elastography are in detail described in "*A Review of Optical Coherence Elastography: Fundamentals, Techniques and Prospects*" IEEE Journal of Selected Topics in Quantum Electronics, Vol. 20, No 2, March/April 2014 which is herein incorporated by reference.

Referring now specifically to FIG. 4*a*, there is shown an excerpt of the medical device 200 for performing compression OCE to determine strain distributed within a silicone sample. The medical device 200 does not comprise a sensing layer and the imaging window of the medical device 200 is brought in direct contact with a surface of the silicone sample 402. For illustrative purposes, the silicone sample 402 is divided into a stiff part 404 and a soft part 406.

The OCE measurement is performed to determine the displacement within the silicone sample 402 using OCT. It should be noted that compression OCE alone cannot quantitatively determine the mechanical property, such as the Young's modulus of the silicone sample 402 as only the strain is determined.

An OCT image (B-scan) of the silicone sample is exemplarily shown in FIG. 4*b* using the medical device 200 without a sensing layer as shown in FIG. 4*b*. As can be seen in the FIG. 4*b*, in this configuration (without the sensing layer) the deformation of the soft part 406 of the silicone sample is restricted by that of the stiff part 404 of the silicone sample 402.

The determined strain along the line 401 is illustrated as a function of the lateral position in FIG. 4*c*. FIG. 4*c* illustrates that the determined strain is substantially constant along the line 401 which extends through the stiff and soft parts 404, 406 of the silicone sample 402. As can be seen in FIG. 4*c*, using the medical device 200 without a sensing layer, it is difficult to locate the interface between the stiff part 404 and the soft part 406 of the silicone sample 402.

In comparison and with reference to FIG. 5*a*, there is shown an excerpt of the medical device 100 as shown in FIG. 1. The medical device 100 shown in FIG. 5a is used to perform a compression OCE measurement to determine the strain distributed within the silicone sample. Simultaneously, stress at a portion of the sensing layer is determined as described with reference to FIG. 1. As the electromagnetic radiation passes through the sensing layer 108, the stress at the sensing layer 108 together with the strain distributed within the silicone sample 402 can be determined from the same OCT image data.

In order to quantitatively determine the mechanical property of the silicone sample 402, such as the Young's modulus, a relation between the determined strain of the silicone sample 402 and the stress that is determined at a portion of the sensing layer 108 is calculated.

In this regard, the medical device 100 is used to determine pressure at lateral positions across an area of the sensing layer 108 as described with reference to FIGS. 1, 2 and 3. In this example, the contact surface of the sensing layer 108 is brought in contact with the surface area of the silicone sample 402 of FIG. 4a.

In this example, the Young's modulus E of the silicone sample is determined as follows:

$$E = \frac{\sigma_{sensing\ layer}}{\varepsilon_{silicone\ sample}}$$

Wherein E relates to the Young's modulus of the silicone sample, $\sigma_{sensing\ layer}$ relates to stress determined at a portion of the sensing layer, and $\varepsilon_{silicone\ sample}$ relates to strain distributed within the silicone sample.

By combining the strain distributed through the silicone sample 402 determined using compression OCE with the stress at the portion of the sensing layer 108, the mechanical property such as the Young's modulus of the silicone sample 402 can be quantitatively determined. In other words, compression OCE is being combined with optical palpation using the medical device 100.

FIG. 5b shows an OCT B-scan of the silicone sample 402 illustrating the variable stress introduced above the stiff and soft regions. The Young's modulus along line 501 in FIG. 5b is shown in FIG. 5c. FIGS. 5b and c demonstrate a difference in elasticity between the stiff and soft parts 404, 406 of the silicone sample 402.

Referring now to FIG. 6 there is shown a medical device 600 in accordance with an embodiment of the present invention. The medical device 600 comprises in this embodiment thimble 602 that is arranged for attachment to a finger 603 of a user. The thimble 602 attaches a sensing component to the finger 603 of the user. The sensing component comprises an optical fibre 604 that includes optical components, which will be discussed further below. The sensing component also includes a sensing layer 606, which corresponds to the sensing layer 108 shown in FIGS. 1a and 1b. In this embodiment the medical device 600 is arranged such that a load is applied to the sensing layer 606 and a material with which the sensing layer 606 is in use is in contact by the finger 603 of the user.

A person skilled in the art will appreciate that in an alternative embodiment the thimble 602 may be replaced with a glove and the sensing component may alternatively be incorporated into one or more finger portions of the glove or in other portions of the glove. Further, the sensing layer 606 may form a portion of the glove.

Figure 6A:
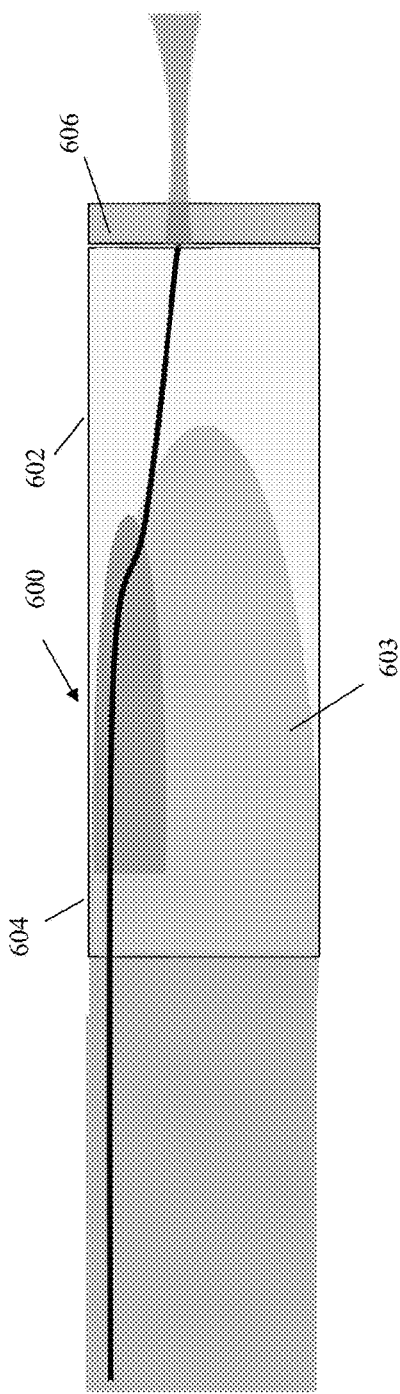
FIGS. 6a and b are schematic representations of a medical device for evaluating a mechanical property of a material in accordance with an embodiment of the present invention.
Figure 6B:
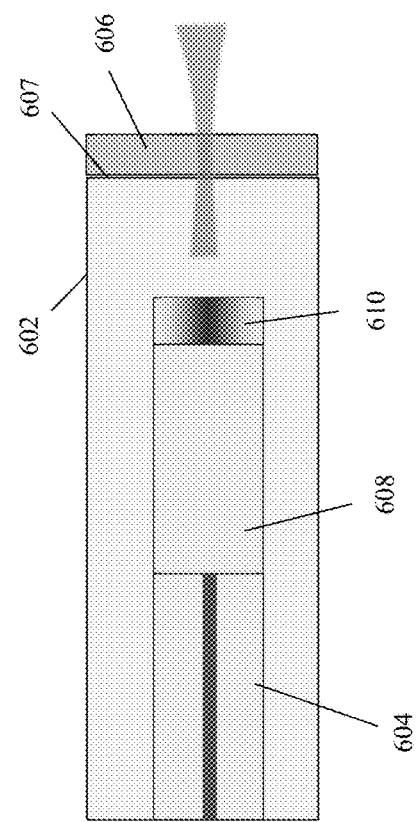

Referring now to FIG. 6b, components of the medical device 600 are shown in more detail. The optical fibre 604 is a single mode fibre and coupled to a "no core" fibre portion 608. The "no core" fibre portion 608 is in turn coupled to a GRIN fibre portion 610, from which in use the electromagnetic radiation is emitted and by which in use the electromagnetic radiation is received. The sensing layer 606 is coupled to the thimble 602 using an optical adhesive 607.

Figure 7B:
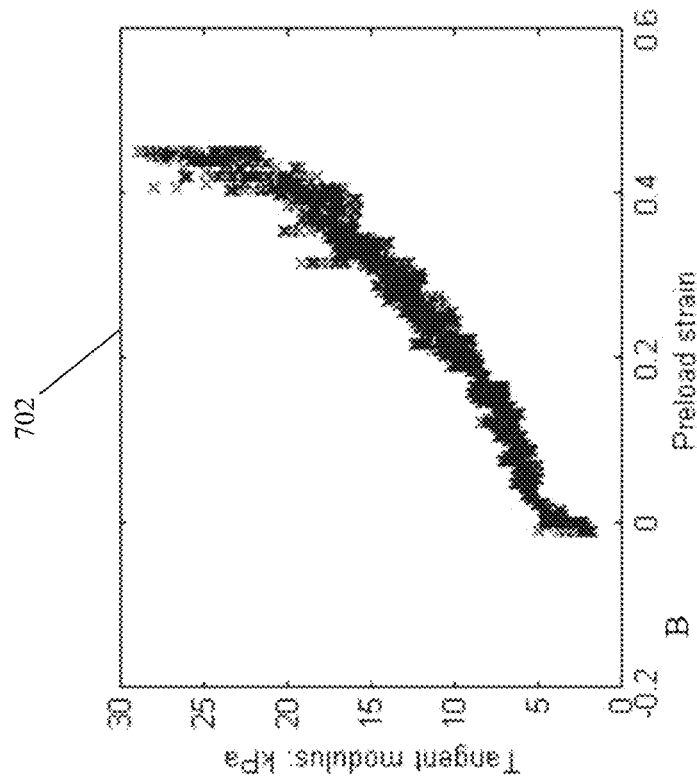
Figure 7A:
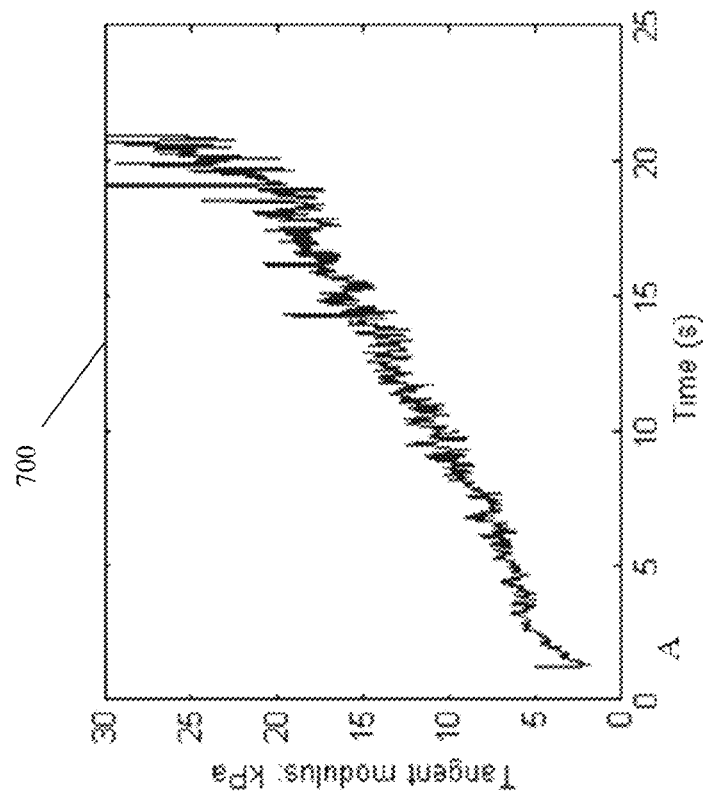

FIGS. 7a and 7b illustrate an example of a result of a stiffness measurement conducted using the device 600 schematically illustrated in FIG. 6a. Plot 700 shows stiffness measured as a function of time and plot 702 shows the measured stiffness as a function of pre-load strain and consequently as a function of deformation of the sensing layer 606.

Figure 8:
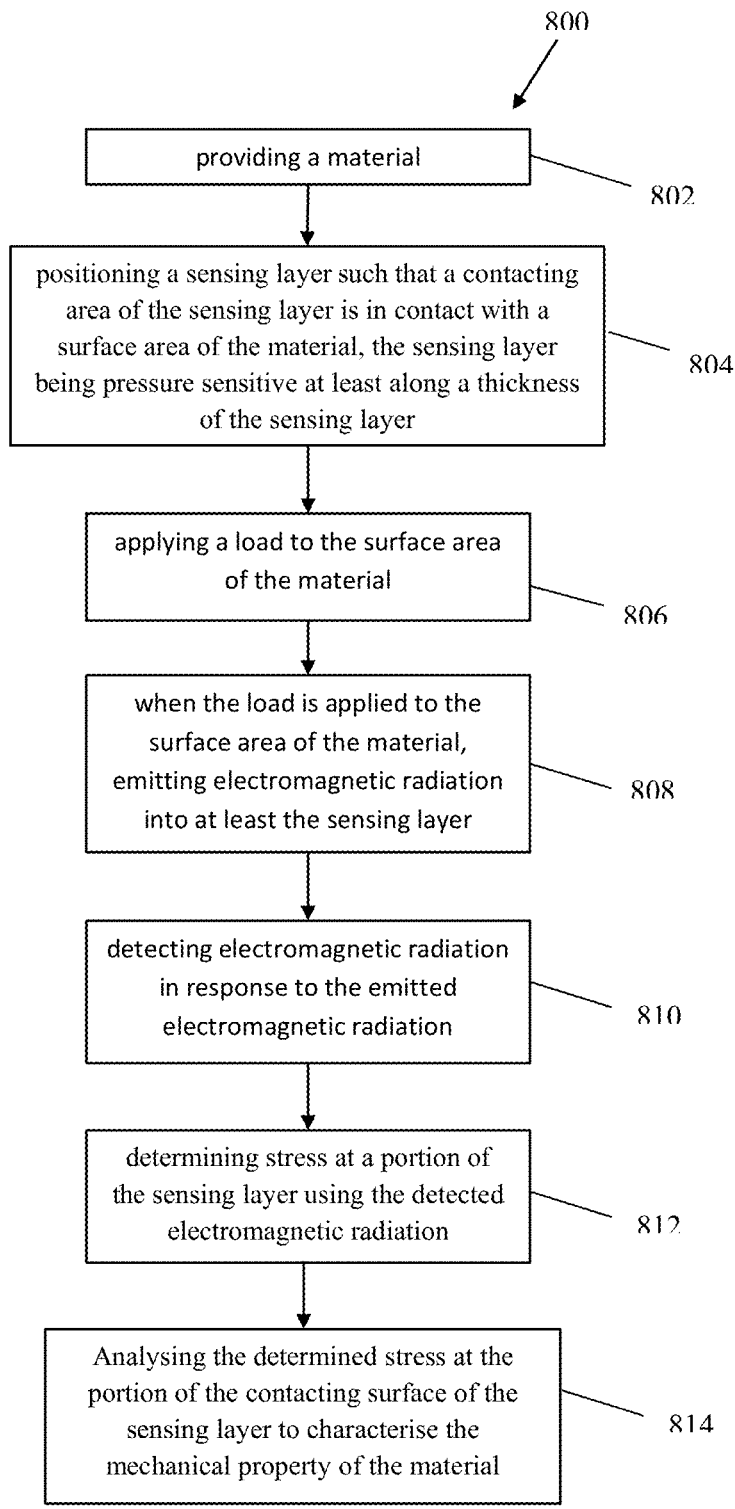
FIG. 8 is a flow chart illustrating a method of evaluating a mechanical property of a material in accordance with an embodiment of the present invention.

Referring now to FIG. 8, there is shown a flow chart illustrating a method 800 in accordance with an embodiment of the present invention.

The method comprises a first step 802 of providing a material. As described above, the material may be biological material such as biological tissue or non-biological material such as silicone material that may be used in the medical field for replicating the form and structure of biological tissue. It will be appreciated that any suitable compliant material is envisaged.

In a next step 804, a sensing layer is positioned such that a contact surface of the sensing layer is in contact with a surface area of the provided material. The sensing layer may for example be the sensing layer 108 of medical device 100 as shown in FIGS. 1a and b. The sensing layer has a property or dimension that is pressure sensitive. In a preferred example, the sensing layer is arranged to conform to a structure of the surface area of the material. For example, the sensing layer may be deformable.

In a further step 806, a load is applied to a portion of the surface area of the material. The load may for example be applied via the sensing layer of the medical device.

When the load is applied to the surface area of the material, electromagnetic radiation is emitted into at least the sensing layer in step 808. The electromagnetic radiation is typically directed towards the surface area of the material, propagating through the sensing layer and into a portion of the material.

In response to the emitted electromagnetic radiation, electromagnetic radiation is detected 810 that has propagated through the sensing layer. For example, the emitted electromagnetic radiation may be deflected or reflected at top and bottom edges of the sensing layer. The detected electromagnetic radiation is subsequently used for determining stress at a portion of the sensing layer in step 812. For example, if the sensing layer is deformed in response to the application of the load, a thickness of the sensing layer may be determined. The thickness of the sensing layer is then used to determine the strain distributed within the sensing layer. With the knowledge of the stress-strain relation of the material of the sensing layer, the stress experienced at a portion of the sensing layer can then be determined.

In a further step, the stress is analysed to evaluate the mechanical property of the provided material. For example, a variation of the mechanical property at lateral positions across an area of the material can be evaluated. It should be noted that by determining the stress at the portion of the sensing layer, the mechanical property of the tissue can only be qualitatively evaluated.

In order to quantitatively determine the mechanical property of the material, such as the Young's modulus which represents the stiffness of the material, the determined stress needs to be combined with an OCE measurement. OCE is typically used to measure the displacement of the material using OCE. In this way, the strain distributed within the material can be determined. By combining the strain of the material with the stress at the sensing layer, the mechanical property of the material can be quantified.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A method of evaluating a mechanical property of a material, the method comprising:
    providing a material;
    positioning a sensing layer at a surface area of the material such that a load can be applied to both at least a portion of the material and at least a portion of the sensing layer at the surface area of the material, the sensing layer having interfaces and a property or dimension that is pressure sensitive;
    applying the load to both at least a portion of the surface area of the material and at least a portion of the sensing layer at the surface area of the material such that the sensing layer deforms;
    emitting electromagnetic radiation into at least a portion of the sensing layer to the interfaces of the layer when the load is applied;
    receiving electromagnetic radiation reflected at the interfaces of the sensing layer;
    determining a thickness of the deformed sensing layer using the electromagnetic radiation reflected at different ones of the interfaces; and
    determining strain at a portion of the sensing layer using the received electromagnetic radiation, the determined strain being indicative of the mechanical property of the material.

2. The method of claim 1 comprising attaching a sensing component to a member using an element for attaching the sensing component such that movement or positioning of the sensing component can be controlled via the member, the sensing component comprising the sensing layer and a receiver for electromagnetic radiation.

3. The method of claim 2 wherein the member is a body portion of a user such that the user wears the element and the sensing component.

4. The method of claim 3 wherein attaching a sensing component to the body portion comprises attaching the sensing component to at a least portion of a hand of a user.

5. The method of claim 3 wherein the step of applying the load comprises applying the load manually through the sensing layer.

6. The method of claim 1 wherein the sensing layer has a known stiffness and the method comprises determining stress from the determined strain.

7. The method of claim 1 wherein the step of determining stress at a portion of the sensing layer comprises determining a deformation of the sensing layer in response to the application of the load and wherein the step of emitting the electromagnetic radiation into at least the sensing layer is conducted such that the electromagnetic radiation is deflected or reflected at a side portion of the sensing layer to determine the thickness of the sensing layer.

8. The method of claim 1 comprising a step of determining strain within the material, and a step of determining a relationship between the determined strain within the material and stress determined for the portion of the sensing layer such that the mechanical property of the material can be quantitatively determined.

9. The method of claim 8 wherein the strain within the material is determined using compression optical coherence elastography (OCE).

10. The method of claim 1 comprising a step of using information in relation to the mechanical property to identify presence or absence of diseased biological tissue.

11. The method of claim 1 wherein the interfaces of the sensing layer comprise top and bottom interfaces of the sensing layer.

* * * * *